United States Patent
Scholz et al.

(10) Patent No.: US 10,232,197 B2
(45) Date of Patent: Mar. 19, 2019

(54) FERMENTED CATIONIC PEPTIDE-BASED ANTIMICROBIAL EXTRACT COMPATIBLE WITH ANIONIC COMPOUNDS

(71) Applicant: Active Micro Technologies, LLC, Lincolnton, NC (US)

(72) Inventors: Durant Scholz, Nanuet, NY (US); Erica Segura, Huntersville, NC (US)

(73) Assignee: Active Micro Technologies, LLC, Lincolnton, NC (US)

( * ) Notice: Subject to any disclaimer, the term of this patent is extended or adjusted under 35 U.S.C. 154(b) by 231 days.

(21) Appl. No.: 14/740,887

(22) Filed: Jun. 16, 2015

(65) Prior Publication Data

US 2015/0366931 A1 Dec. 24, 2015

Related U.S. Application Data

(60) Provisional application No. 62/013,669, filed on Jun. 18, 2014.

(51) Int. Cl.
| | |
|---|---|
| *A61K 8/64* | (2006.01) |
| *A61K 8/99* | (2017.01) |
| *C07K 17/02* | (2006.01) |
| *A61Q 19/00* | (2006.01) |
| *A61K 8/73* | (2006.01) |
| *A61K 35/747* | (2015.01) |

(52) U.S. Cl.
CPC ............... *A61Q 19/00* (2013.01); *A61K 8/64* (2013.01); *A61K 8/73* (2013.01); *A61K 35/747* (2013.01); *A61K 2800/10* (2013.01); *A61K 2800/48* (2013.01); *A61K 2800/524* (2013.01); *A61K 2800/85* (2013.01)

(58) Field of Classification Search
None
See application file for complete search history.

(56) References Cited

U.S. PATENT DOCUMENTS

| | | | | |
|---|---|---|---|---|
| 7,550,430 | B2 * | 6/2009 | Keeler | ............................ 514/1.1 |
| 2005/0196480 | A1 * | 9/2005 | Sullivan | ................... A61K 8/99 |
| | | | | 424/780 |
| 2007/0264394 | A1 | 11/2007 | Dutreux et al. | |

OTHER PUBLICATIONS

Uteng et al., Applied and Environmental Microbiology, 2002, 68(2), 952-956.*
Todorov, et al., "Comparison of Two Methods for Purification of Plantaricin ST31, A Bacteriocin Produced by Lactobacillus Plantarum ST31," Braz. J. Micro. 35:157-160 (2004).*
Leucidal™ Liquid SF, Activemicro Technologies, Technical dossier, pp. 1-156, accessed Sep. 4, 2017 at URL activemicrotechnologies.com/product/.*
Jungbauer et al., "Ion-exchange Chromatography," Meth. Enz. 463:349-371 (2009)).*
Chinachoti N. et al. <<Bioreactor systems for efficient production and separation of nisin Z using Lactococcus lactis IO-1 [Mar. 1998]>>, Journal of the Faculty of Agriculture, Kyushu University, 2001, vol. 42, No. 3-4, abstract.
Uteng M. et al. <<Rapid Two-Step Procedure for Large-Scale Purfication of Pediocin-Like Bacteriocins and Other Cationic Antimicrobial Peptides from Complex Culture Medium>>, Applied and Environmental Microbiology, 2002, vol. 68, No. 2, pp. 952-956.
Bagheri M. et al. <<Immobilization Reduces the Activity of Surface-Bound Cationic Antimicrobial Peptides with No Influence upon the Activity Spectrum>>, Antimicrobial agents and chemotherapy, 2009, vol. 53, No. 3, p. 1132-1141.
Cho Won_Mi et al. <<Design and synthesis of novel antibacterial peptide-resin conjugates>>, Bioorganic & Medicinal Chemistry Letters, 2007, vol. 17, p. 5772-5776.
Oh Sejong et al. <<Effect of bacteriocin produced by Lactococcus sp. HY 449 on skin-inflammatory bacteria>>, Food and Chemical Toxicology, 2006, vol. 44, p. 552-559.
Shanova, O., International Search Report for PCT/US2015/36218, dated Oct. 22, 2015, Moscow, Russia.

* cited by examiner

*Primary Examiner* — Julie Ha
*Assistant Examiner* — Kristina M Hellman
(74) *Attorney, Agent, or Firm* — Lerner, David, Littenberg, Krumholz & Mentlik, LLP

(57) ABSTRACT

An antimicrobial composition compatible with anionic compounds is prepared by a process of contacting a cationic peptide-based antimicrobial extract with an ion exchange resin.

3 Claims, 2 Drawing Sheets

FERMENTED CATIONIC PEPTIDE-BASED ANTIMICROBIAL EXTRACT COMPATIBLE WITH ANIONIC COMPOUNDS

BACKGROUND OF THE INVENTION

Peptide-based antimicrobials are well-known in the art. They are used in several industries such as personal care products, water treatment, food applications, and medicine and healthcare. For example, in personal care products, antimicrobials are used to help retard or eliminate the growth of topical pathogens as well as to preserve the personal care products from spoiling or to substantially improve the shelf-life of a product. The antimicrobials can also be used to preserve the function of various active ingredients including anti-oxidants (vitamins), emulsifiers, and surfactants.

Previous peptide-based antimicrobials have all been primarily cationic in nature. As a result, they are incompatible with anionic products due to charge interaction. This incompatibility can result in a loss of antimicrobial activity, or in the case of anionic thickeners, a loss of viscosity and clarity.

Thickeners are materials used in the cosmetics industry to increase the viscosity of a product. They play a vital role in maintaining lather quality, delivery of active ingredients (referred to as "actives") and suspending insoluble ingredients, among others, and are usually used in small quantities (<1%). They are mostly categorized by their origin; the natural polymers have plant, animal or microbial origins, hence their chemical structures are based on proteins or polysaccharides. Examples include Xanthan Gum. The use of those polymers is limited by pH, temperature, solubility and the presence of cations in the system.

The synthetic polymers are acrylic acid-based polymers widely used in small quantities within the cosmetics industry. Acrylic acid polymers are anionic hydrogels capable of swelling but do not dissolve in water. For swelling to occur, the polymers have to be neutralized using a base to form a water soluble salt. Polyacrylic acids are highly sensitive to electrolytes. Examples include carbomers, where base neutralization introduces negatively charged carboxyl groups to the polymer backbone which causes the carbomer to uncoil as a result of the increased repulsive forces. As carbomers are anionic in nature, they are incompatible with cations, creating problems if carbomers must be used in a formulation containing any of the aforementioned excipients, such as cationic antimicrobials. While the application discusses thickeners as an example, it should be appreciated that the application is directed to the compatibility of cationic antimicrobial peptides with anionic compounds as a whole, including, but not limited to, thickeners and surfactants.

Accordingly, there is a clear need for a peptide-based antimicrobial with enhanced activity and cationic-anionic compatibility for use in cosmetics, food, and beverages.

BRIEF SUMMARY OF THE INVENTION

This need is addressed by a peptide-based antimicrobial compound with and cationic-anionic compatibility.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
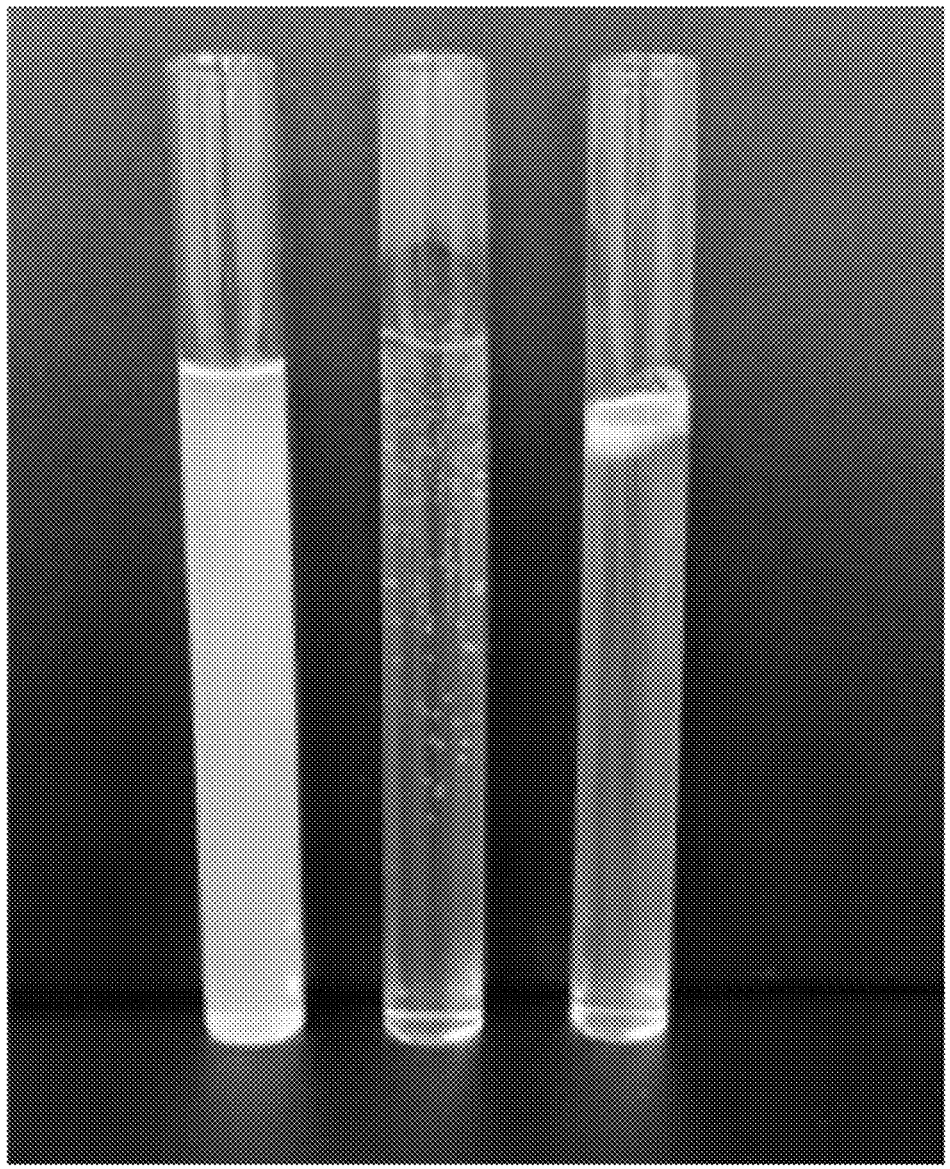
FIG. 1 shows the results of a compatibility test between an extract of the current invention with anionic thickeners.

It is known that fermentation of biomass using certain Gram-positive bacterial species, such as *Lactobacillus*, produces an antimicrobial agent that can be used to protect cosmetic and food or beverage products against contamination. Those products are traditionally incompatible with anionic materials, rheological agents in particular, due to their primarily cationic or positively charged nature. It is noted that using the commonly-accepted definitions, "cation" or "cationic" refers to a positively charged ion and "anion" or "anionic" refers to a negatively charged ion.

Previous lab tests with iterations of *Lactobacillus* ferment have all been incompatible with anionic systems, regardless of the efforts to remove or mask that cationic charge. In these instances there is either a loss of antimicrobial activity and/or a loss in viscosity and clarity. The antimicrobial activity of the *Lactobacillus* ferment byproduct is due to the presence of cationic peptides (Savadogo, A., et al. 2004. Pakistan Journal of Nutrition 3:174-79; Hastings, J. W., et al. 1991. Journal of Bacteriology 173: 7491-500; Fleury, Y., et al. 1996. Journal of Biological Chemistry 271: 14421-29). It is the interaction of these cationic peptides binding with the anionic materials that result in the overall incompatibility.

In general, the present invention may include an extract resulting from the fermentation of an antimicrobial product such as *Lactobacillus*, treated with an ion exchange resin so that it is completely compatible with anionic surfactants and thickeners. One non-limiting example of such a treated extract is Leucidal®Liquid SF treated with USF C-211 Cationic Resin ("C-211 Resin"), which is an example of a strong acid cation exchange resin. The term "strong acid" refers to an acid that completely ionizes (dissociates) in a solution. The treated extract also has comparable or improved antimicrobial activity compared to non-treated extract. The extract is cationic in nature, retains its antimicrobial activity and has excellent compatibility with anionic compounds. This is unexpected, since other cationic antimicrobial products either lose their antimicrobial efficacy, or are incompatible with anionics, or both. As used herein, the term "compatible with anionic products" means that there is not a significant loss of antimicrobial activity, or in the case of anionic thickeners, a significant loss of viscosity and/or clarity. While the present application uses Leucidal®Liquid SF treated with C-211 Resin as a primary example of the extract of the present invention, it should be appreciated that this is just one example and that other resins, such as Amberlite IR-120B, Generik S-8, Source 30S, and SP Sepharose Fast Flow, may be used in place of the C-211 Resin.

The extract comes from select *Lactobacillus* bacteria which is fermented in defined media under controlled pH, temperature, and time conditions. A specified enzymatic compound is then added to initiate controlled cell lysis, followed by filtration to remove any undesired plant and/or biotic matter.

Water treatment facilities have traditionally removed charged particles to soften or purify desired products. This is performed using ion exchange materials which are insoluble acids or bases that contain designated salts. The insolubility and charge capacity enables the material to exchange cations (positively charged ions) or anions (negatively charged ions). Until now, utilization of such exchangers to remove charged molecules from solution has not been used to resolve issues such as antimicrobial activity or incompatibility with oppositely charged systems.

Unexpectedly we have found that treatment of these types of *Lactobacillus* ferment peptide products with ion exchange resin eliminates all incompatibility with anionic systems without reducing the antimicrobial activity of the product. The exchange material works synergistically with the fermented antimicrobial product to alter its charged state without affecting the active peptide structure, but enough so to eliminate any incompatibility issues typically seen as loss of viscosity or clarity. This results in an active cationic antimicrobial peptide that can be used with any rheological agent or anionic material to produce a clear, viscous, and effective bactericidal product. Treatment of the extract may be carried out by contacting the resin with the extract, in a batch or continuous process.

Testing

A compatibility test was conducted to evaluate the behavior of the extract of the current invention compared with a negative control Leucidal®Liquid SF with no C-211 Resin treatment, with common thickeners such as Keltrol® CG-SFT, Carbopol®Ultrez 10 and Carbopol® 940 used in the cosmetic and personal care industry. For purposes of this testing, the extract was Leucidal®Liquid SF treated with C-211 Resin. Different parameters were considered to determine the effectiveness of the C-211 Resin treatment to make Leucidal®Liquid SF compatible with the anionic thickeners.

The thickeners were tested at a specific concentration. The appearance and viscosity changes were evaluated as compatibility test parameters after the addition of the Leucidal®Liquid SF, where a clear gel with no presence of white spots suspended and the higher viscosity values measured with Brookfield viscometer demonstrate the compatibility between the testing agents.

Under the conditions of this assay, the extract was considered compatible with Keltrol® CG-SFT, Carbopol®Ultrez 10 and Carbopol® 940. Leucidal®Liquid SF with no C-211 Resin treatment was considered incompatible with Keltrol® CG-SFT, Carbopol®Ultrez 10 and Carbopol® 940.

The materials used in the testing include:
Beakers 200 ml
Overhead mixer
Brookfield Viscometer
pH Meter
Sodium Hydroxide 25% (v/v)
Sodium Hydroxide 18% (v/v)
Scale
Test Tubes

TABLE 1

Tested Thickeners

| Trade Name | INCI Name | Manufacturer |
|---|---|---|
| KETROL CG-SFT | Xanthan Gum | CPKelco |
| CARBOPOL Ultrez 10 | Carbomer | Lubrizol |
| CARBOPOL 940 | Carbomer | Lubrizol |

The tested solutions include:
Leucidal®Liquid SF with C-211 Resin treatment Lot Number 35252.
Leucidal®Liquid SF with no C-211 Resin treatment Lot Number NC140415-B (Negative Control).

The method used for the compatibility test is as follows:
1. Calculate the amounts of each solution with the percentages given for each thickener:

TABLE 2

KETROL CG-SFT Concentration Used in Compatibility Test

| Compound | % |
|---|---|
| Water | 95.5% |
| LEUCIDAL Liquid SF | 4.0% |
| KELTROL CG-SFT | 0.5% |

TABLE 3

CARBOPOL Ultrez 10 Concentration Used in Compatibility Test

| Compound | % |
|---|---|
| Water | 95.8% |
| LEUCIDAL Liquid SF | 4.0% |
| CARBOPOL Ultrez 10 | 0.2% |

TABLE 4

CARBOPOL 940 Concentration Used in Compatibility Test

| Compound | % |
|---|---|
| Water | 95.8% |
| LEUCIDAL Liquid SF | 4.0% |
| CARBOPOL 940 | 0.2% |

2. Mix Leucidal®Liquid SF and Water until the solution is uniform.
3. Add the thickener and mix at high speed for 30 min-1 hour.
4. Check the pH for Carbopol®Ultrez 10 and Carbopol®Ultrez 940 solutions and raise it until 6.0-7.0 using Sodium Hydroxide 25% (v/v) for Carbopol®Ultrez 10 and Sodium Hydroxide 18% (v/v) for Carbopol® 940.
5. Check the appearance parameters of each solution: clarity and particles suspended.
6. Measure the viscosity of each solution using a Brookfield viscometer as following, using as a positive control the thickener with no Leucidal®Liquid SF in it to have a starting point.

TABLE 5

Viscosity Measure Parameters

| Thickener | Brookfield Model and Spindle | rpm |
|---|---|---|
| KELTROL CG-SFT | LV-1 | 60 |
| CARBOPOL Ultrez 10 | RVT-D | 2 |
| CARBOPOL 940 | RVT-D | 2 |

7. Take photographs of the appearance results and register the viscosity values results.

For the test solution to be evaluated as compatible with Keltrol® CG-SFT, Carbopol®Ultrez 10 and Carbopol® 940 there must show a clear gelatin or gel with no particles suspended and a high viscosity value than the negative control.

Results

Appearance

Figure 2:
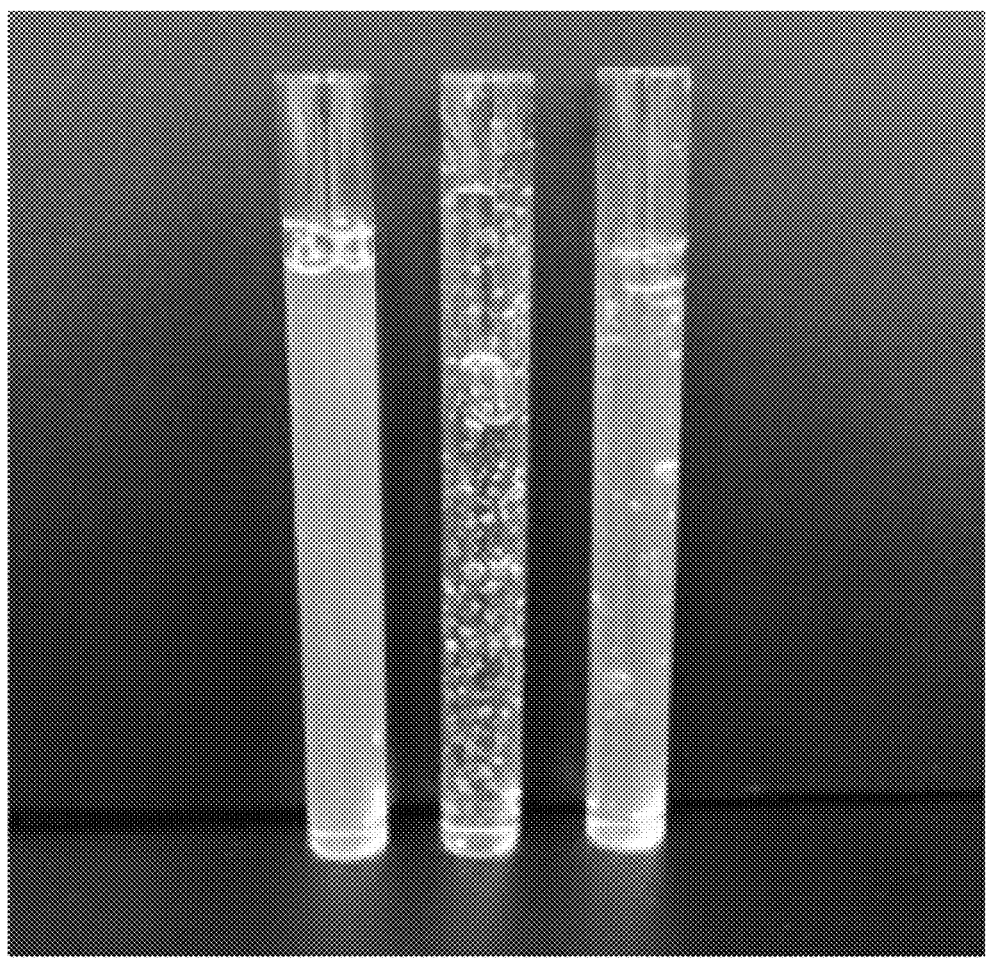
FIG. 2 shows the results of a compatibility test between a negative control and the anionic thickeners.

Referring to FIGS. 1 and 2, the compatibility test results with Keltrol® CG-SFT, Carbopol®Ultrez 10 and Carbopol® 940 are shown, sequentially from left to right in the views. In FIG. 1, the clarity of the gels and the absence of white spots suspended demonstrate that the extract (35252) is compatible with the thickeners tested, making a uniform thicker solution. The xanthan gum solution is slightly hazier than the others, but this is a normal appearance for this grade of Keltrol®. In FIG. 2, the haziness and the presence of white spots suspended along with bubbles through the thickener solution demonstrated that the negative control Leucidal®Liquid SF no C-211 Resin treatment (NC140415-B) is incompatible.

Viscosity Values

The viscosity was measured using a Brookfield viscometer, where Keltrol® CG-SFT, Carbopol®Ultrez 10 and Carbopol® 940 with the extract (35252) showed higher viscosity values than Keltrol® CG-SFT, Carbopol®Ultrez 10 and Carbopol® 940 with the negative control Leucidal®Liquid SF no C-211 Resin treatment (NC140415-B) under the conditions of this assay.

TABLE 6

Viscosity Values for KELTROL CG-SFT, CARBOPOL Ultrez 10 and CARBOPOL 940 with LEUCIDAL Liquid SF C-211 resin treated (35252) and control LEUCIDAL Liquid SF no C-211 resin treatment (NC140415-B)

| Thickener | Positive Control | 35252 (Treated) | NC140415-B Negative Control |
|---|---|---|---|
| KELTROL CG-SFT Brookfield LV-3, 60 rpm | 291.9 cP | 212.0 cP | 104.3 cP |
| CARBOPOL Ultrez 10 Brookfield RVT-D, 2 rpm | 77,000 cP | 80,000 cP | 14,000 cP |
| CARBOPOL 940 Brookfield RVT-D, 2 rpm | 75,000 cP | 69,000 cP | 14,000 cP |

All criteria for a valid study were met as described in the protocol. The results of the compatibility test for the anionic agents Keltrol® CG-SFT, Carbopol®Ultrez 10 and Carbopol® 940 with the cationic extract demonstrate that the treatment helps with the electrolyte issues between anionic and cationic agents.

Additionally, inhibition activity and zone of inhibition tests were performed. The results of the inhibition studies are shown in Tables 7 and 8.

TABLE 7

Inhibition Activity Data

| | Minimum Inhibitory Concentration (%) | |
|---|---|---|
| Organism (ATCC #) | NC140415-B | 35252 (Treated) |
| E. coli #8379 | 0.5 | 0.5 |
| S. aureus #6538 | 0.5 | 0.5 |
| P. aeruginosa #9027 | 0.5 | 0.5 |
| C. albicans #10231 | 0.5 | 0.5 |
| A. brasiliensis #16404 | 0.5 | 0.5 |

TABLE 8

Zone of Inhibition Test

| | Zone of Inhibition (mm) | | | |
|---|---|---|---|---|
| | NC140415-B | | 35252 (Treated) | |
| Organism (ATCC #) | 4% | 100% | 4% | 100% |
| E. coli #8379 | 0 | 4 | 0 | 12 |
| S. aureus #6538 | 14 | 22 | 14 | 22 |
| P. aeruginosa #9027 | 0 | 8 | 0 | 8 |
| C. albicans #10231 | 12 | 25 | 14 | 30 |
| A. brasiliensis #16404 | 10 | 15 | 14 | 19 |

The foregoing has described a fermented cationic peptide-based antimicrobial extract compatible with anionic compounds. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A composition comprising:
   an anionic compound selected from the group consisting of polyacrylic acids and carbomers; and
   a treated cationic peptide-based antimicrobial extract comprising:
   a fermentation byproduct of *Lactobacillus* bacteria and a cationic ion exchange resin;
   wherein the treated cationic peptide-based antimicrobial extract has improved antimicrobial activity in comparison to an untreated cationic peptide-based antimicrobial extract comprising a fermentation byproduct of *Lactobacillus* bacteria when both are combined with an anionic material.

2. A method of making a composition comprising:
   treating a cationic peptide-based antimicrobial extract with a cationic ion exchange resin, wherein the cationic peptide-based antimicrobial extract is a fermentation byproduct of *Lactobacillus* bacteria to form an antimicrobial composition; and
   maintaining a cationic charge on the antimicrobial composition; and
   combining the antimicrobial composition with an anionic compound selected from the group consisting of polyacrylic acids and carbomers,
   wherein the antimicrobial composition has improved antimicrobial activity and rheological activity in comparison to an untreated cationic peptide-based antimicrobial extract comprising a fermentation byproduct of *Lactobacillus* bacteria when both are combined with an anionic material.

3. The method according to claim 2, wherein the ion exchange resin is a strong acid cationic resin.

\* \* \* \* \*